United States Patent [19]

Kwentus et al.

[11] Patent Number: 4,501,907

[45] Date of Patent: Feb. 26, 1985

[54] MALEIC ANHYDRIDE PRODUCTION USING HIGH BUTANE FEED CONCENTRATION

[75] Inventors: Gerald K. Kwentus, Pensacola, Fla.; Michael Suda, St. Louis, Mo.

[73] Assignee: Monsanto Company, St. Louis, Mo.

[21] Appl. No.: 451,118

[22] Filed: Dec. 20, 1982

[51] Int. Cl.$^3$ .......................................... C07D 307/60
[52] U.S. Cl. .................................... 549/259; 549/260
[58] Field of Search ............................... 549/259, 260

[56] References Cited

U.S. PATENT DOCUMENTS 3,293,268  12/1966  Bergman et al. ................ 260/346.8
3,832,359   8/1974  Freerks et al. ................... 260/346.8
4,002,630   1/1977  Bremer et al. ................... 260/346.8 A

*Primary Examiner*—Henry R. Jiles
*Assistant Examiner*—Bernard I. Dentz
*Attorney, Agent, or Firm*—Wendell W. Brooks; James C. Logomasini; Arnold H. Cole

[57] ABSTRACT

An improvement in a process for the production of maleic anhydride by the catalytic vapor phase oxidation of a saturated aliphatic hydrocarbon having 4–10 carbon atoms in the presence of a catalyst comprising phosphorus, vanadium and oxygen, wherein long reactor tubes are used in a process employing a high feed concentration and low space velocity so as to minimize air compression.

6 Claims, No Drawings

MALEIC ANHYDRIDE PRODUCTION USING HIGH BUTANE FEED CONCENTRATION

BACKGROUND OF THE INVENTION

A. Field of the Invention

This invention relates to a method for the preparation of maleic anhydride by the catalytic vapor phase oxidation of saturated hydrocarbons.

B. The Prior Art

Maleic anhydride is of significant commercial interest throughout the world. It is used alone or in combination with other acids in the manufacture of alkyd and polyester resins. It is also a versatile intermediate for chemical sythesis. Significant quantities of maleic anhydride are produced each year to satisfy these needs. The prior art discloses a number of processes used in the conversion of organic feed stocks to maleic anhydride.

U.S. Pat. No. 3,293,268 teaches the process of oxidizing saturated aliphatic hydrocarbons to maleic anhydride under controlled temperature conditions and in the presence of phosphorus-vanadium-oxygen catalyst. A variety of reactors have been found to be useful and the most commonly used commercial reactor is a multiple tube heat exchanger type reactor. The tubes of such reactors, according to the prior art, vary in diameter from 0.635 centimeters to about 7.62 centimeters and the length varies from about 1 meter to about 3 meters or more. The oxidation is an exothermic reaction and therefore a relatively close control of reaction temperature must be maintained. It is known to be desirable to have the surface of the reactor at a relatively constant temperature and some medium to conduct heat from the reactor is necessary to aid temperature control. The preferred reaction temperature is about 450° C. Temperature control may be effected by the use of mercury, molten lead and the like, but it has been found that eutectic salt baths have been most satisfactory for temperature control. One such salt bath is a sodium nitrate-sodium nitrite-potassium nitrate eutectic mixture. An additional method of temperature control is to use a metal block reactor whereby the metal surrounding the tube acts as a temperature regulating body. The heat exchange medium is kept at the proper temperature by heat exchangers and the like. The reactor or reaction tubes have been fabricated of iron, stainless steel, carbon steel, glass and the like. Some reactors contain a preheat zone containing an inert material such as ¼ inch aluminum oxide pellets, inert ceramic balls, nickel balls or chips and the like.

The fixed tube reactor has not achieved the lower air compression costs per unit of maleic anhydride of a fluid bed reactor due to heat transfer limitations in a conventional fixed tube reactor and a short reaction time in the reactor tubes.

It is an object of this invention to lower air compression costs by increasing the length of the reactor tubes, the concentration of the reactants, and the reaction time.

SUMMARY OF THE INVENTION

The improvement comprises, in conjunction with the employment of a feed concentration of butane to air, about 3-5% by volume and a dilution of the upstream portion of the catalyst pack to the extent necessary to prevent hot spot runaway, the use of a reactor tube of a sufficient length, consistent with inside diameter and air flow space within the catalyst packing to permit a single pass conversion of at least about 70% of butane fed to the reactor. Under ordinary circumstances, reactor tubes in accordance with this invention are 5-12 meters long. An optional step provides for packing the upstream head of the reactor and all upstream ducts through which butane-air mixtures flow with high surface area low bulk density inert solids so as to prevent deflagration of the butane air mixture.

DETAILED DESCRIPTION OF THE INVENTION

As indicated above, reactor efficiency is improved by employing a feed concentration of butane to air of about 3-5% by volume. In order to use such a high concentration of butane, the upstream portion of the catalyst pack is diluted with inert solids, larger pellets, less active catalyst and the like to prevent hot spots. Reactor tubes are employed which are long enough to permit a single pass conversion of at least about 70% of the butane fed to the reactor. In order to prevent an excessive pressure drop within the reactor tube, or an excess of pressure feeding the tube, there must be a sufficient air flow space through the catalyst pack. As is well known in the art, air flow depends in part upon the diameter of the tube and in part upon the size and shape of the catalyst masses in the pack.

COMPARATIVE EXAMPLES 1-5

Pellets of phosphorous vanadium oxygen catalyst were charged to a reactor having a charge length of 5.79 meters, an outside diameter of 1.0", and inside diameter of 0.834". The weight of the charge was 1217.5 grams. Charging temperature was 200° C. No inerts or other dilution methods were used. The reactor was started up on butane at a feed concentration of 1.5 percent and then run for a period of 2913 hours. During that time, the conditions were adjusted as shown in the following table where $T_b$ is bath temperature and $T_R$ is reactor temperature.

TABLE I

| Ex | Feed Conc. % | $T_b$ C | $T_R$ C | $P_{in}$ psig | SV $hr^{-1}$ | Yield % | Prod. lb/hr-$ft^3$ | Hrs |
|---|---|---|---|---|---|---|---|---|
| 1 | 1.51 | 425 |  | 15.0 | 1145 | 55.1 | 2.45 | 172 |
| 2 | 2.01 | 431 |  | 15.0 | 1161 | 51.4 | 3.09 | 774 |
| 3 | 3.98 | 416 | 457 | 10.7 | 359 | 49.7 | 1.83 | 2481 |
| 4 | 4.00 | 414 | 423 | 10.7 | 357 | 47.5 | 1.76 | 2693 |
| 5 | 3.99 | 389 | 436 | 10.7 | 358 | 39.7 | 1.47 | 2913 |

A hot spot problem was encountered at 2484 hours.

EXAMPLES 6-10

The catalyst was of the type described in Example 1, but had been activated at low feed concentrations The catalyst pack was diluted with inert aluminum oxide pellets as follows: For the first 4 feet of the pack, 40 volume percent inerts; for the next 4 feet of the pack, 20 percent inerts; and for the remainder of the pack, 0 percent inerts. The reactor tube was the same as described in Example 1 except that the length of the charge was 6.096 meters. The catalyst was charged to the tube at 200° C., and started up on butane according to the conditions described for Example 1. The results given in Table II were obtained.

TABLE II

| Ex | Butane Feed Conc. % | $T_b$ C | $T_R$ C | $P_{in}$ psig | SV $hr^{-1}$ | Yield % | Prod. lbs/hr -ft$^3$ | Hrs |
|---|---|---|---|---|---|---|---|---|
| 6 | 3.48 | 403 | 426 | 10.7 | 364 | 47.8 | 1.57 | 119 |
| 7 | 4.01 | 421 | 441 | 10.7 | 364 | 47.9 | 1.81 | 1102 |
| 8 | 4.01 | 428 | 448 | 10.7 | 535 | 43.8 | 2.42 | 1508 |
| 9* | 2.01 | 427 | 434 | 17.7 | 529 | 57.0 | 1.57 | 3132 |
| 10 | 4.01 | 440 | 457 | 10.7 | 365 | 49.3 | 1.86 | 6393 |

*comparative

In the above examples with the diluted catalyst pack there were no hot spot problems.

EXAMPLES 11-15

The catalyst was of the type described in Examples 1-10. Dilution was like that described in Examples 6-10. In this case, the catalyst was activated as a diluted bed under low space velocities. Bed length was 6.096 meters. Conditions and results are described in Table III.

TABLE III

| Ex | Butane Feed Conc. % | $T_b$ C | $T_R$ C | $P_{in}$ psig | SV $hr^{-1}$ | Yield % | Prod. lb/hr -ft$^3$ | Hours |
|---|---|---|---|---|---|---|---|---|
| 11* | 2.00 | 410 | 427 | 10.7 | 263 | 63.6 | 1.19 | 371 |
| 12 | 3.00 | 423 | 451 | 10.7 | 366 | 56.8 | 1.61 | 822 |
| 13 | 4.02 | 431 | 455 | 10.7 | 368 | 49.6 | 1.90 | 1660 |
| 14 | 4.30 | 435 | 455 | 10.7 | 371 | 47.1 | 2.52 | 3078 |
| 15 | 4.32 | 436 | 460 | 10.7 | 536 | 41.8 | 2.50 | 3266 |

*Comparative

In the above examples with the diluted catalyst pack there were no hot spot problems.

We claim:

1. In a process for producing maleic anhydride by the catalytic vapor phase oxidation of butane, in the presence of a catalyst comprising phosphorus, vanadium and oxygen, the reaction being conducted in a fixed bed tube-type reactor packed with catalyst, the improvement comprising in combination (1) employing a feed concentration of butane to air of about 3-5% by volume at a space velocity from about 364 $hr^{-1}$ to about 536 $hr^{-1}$; (2) diluting the upstream portion of the catalyst pack to the extent necessary to prevent hot spot runaway; and (3) using a reactor tube of sufficient length, consistent with inside diameter and air flow space within the catalyst packing to permit a single pass conversion of at least about 70% of butane fed to the reactor.

2. The process improvement of claim 1 wherein the reactor tubes are 5-12 meters in length.

3. The process improvement of claim 1 wherein the reactor tubes are 5-6 meters in length.

4. The process improvement of claim 1 further including packing the upstream head of the reactor and all upstream ducts through which butane-air mixtures flow with high surface area low bulk density inert solids so as to prevent deflagration of the butane.

5. The process improvement of claim 1 wherein the upstream portion of the catalyst pack is diluted with inert solids.

6. The process improvement of claim 5 wherein the inert solids comprise aluminum oxide.

* * * * *